US009765027B2

(12) United States Patent
Vardanyan et al.

(10) Patent No.: US 9,765,027 B2
(45) Date of Patent: Sep. 19, 2017

(54) SUBSTITUTED 1-ARYLETHYL-4-ACYLAMINOPIPERIDINE DERIVATIVES AS OPIOID/ALPHA-ADRENORECEPTOR MODULATORS AND METHOD OF THEIR PREPARATION

(71) Applicant: The Arizona Board of Regents on Behalf of the University of Arizaona, Tucson, AZ (US)

(72) Inventors: Ruben S. Vardanyan, Tucson, AZ (US); Victor J. Hruby, Tucson, AZ (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 14/834,185

(22) Filed: Aug. 24, 2015

(65) Prior Publication Data
US 2016/0052882 A1   Feb. 25, 2016

Related U.S. Application Data

(60) Provisional application No. 62/040,886, filed on Aug. 22, 2014.

(51) Int. Cl.
C07D 211/58   (2006.01)
(52) U.S. Cl.
CPC .................................. C07D 211/58 (2013.01)
(58) Field of Classification Search
CPC .................................................. C07D 211/58
USPC ........................................ 546/223, 224, 226
See application file for complete search history.

(56) References Cited

U.S. PATENT DOCUMENTS

| 4,029,801 | A |   | 6/1977  | Cavalla et al. ............... 424/267 |
|-----------|---|---|---------|---------------------------------------|
| 4,304,911 | A | * | 12/1981 | Zenitz ..................... C07C 29/14 |
|           |   |   |         | 544/130                               |
| 4,649,144 | A |   | 3/1987  | Matsumoto et al.                      |
| 2004/0147503 | A1 |  | 7/2004 | Zipfeil                               |

FOREIGN PATENT DOCUMENTS

| WO | 2007058482 A1 | 5/2007  |                |
|----|---------------|---------|----------------|
| WO | WO2012089738  | 7/2012  | ..... A61K 9/00 |
| WO | WO2012149113  | 11/2012 | ..... A61K 31/485 |

OTHER PUBLICATIONS

Archibald "Piperidine derivatives" CA85:21127 (1976).*
Archibald et al. "Piperidine . . . " CA85:21127 (1976).*
Hamaguchi et al. "Preparation of . . . " CA157:356571 (2012).*
Imazaki et al. "Preparation of hetero . . . " CA138:39295 (2002).*
Klaveness et al "Preparation of (hetero) . . . " CA143:115451 (2005).*
Improper Markush, Fed. Reg. 76(27) 7162-75, slide 1, 64-67 (2011).*
Archibald et al. "Benzamidopiperidines . . . " CA81:114406 (1974).*
Archibald et al. "Benzaidopiperidines . . . " J. Med. Chem. 17&7) 739-744 (1974).*
Invitation to Pay Additional Fees issued in application No. PCT/US2015/046585, dated Nov. 2, 2015 (2 pgs).
Anon, N.Z., Alvimopan: ADL 8-2698, ADL 82698, entrareg, LY 246736, Drugs in R&D, (2006), 7(4), 245-253 (10 pgs).
Boothby, L.A.,Doering, P.L., Buprenorphine for the treatment of opioid dependence, Am. J. Health-System Pharm., (2007), 64(3), 266-272 (7 pgs).
Bosco, D.; Plastino, M.; Colica, C.; Bosco, F.; Arianna, S.; Vecchio, A.; Galati, F.; Cristiano, D.; Consoli, A.; Consoli, D., Opioid Antagonist Naltrexone for the Treatment of Pathological Gambling in Parkinson Disease, Clinical Neuropharmacology (2012), 35(3), 118-120 (3 pgs).
Brefel-Courbon, C.; Thalamas, C.; Paul, H. P. S.; Senard, J-M.; Montastruc, J-L.; Rascoi, O., α2-Adrenoceptor antagonists. A new approach to Parkinson's disease? CNS Drugs (1998), 10(3), 189-207 (19 pgs).
Buck, K.; Ferger, B., The selective α1 adrenoceptor antagonist HEAT reduces L-DOPA-induced dyskinesia in a rat model of Parkinson's disease, Synapse (2010), 64(2), 117-126 (10 pgs).
Capasso, A., D'Ursi, A., Pharmacological activity of new mu, k, delta receptor agonists and antagonists. Studies in Natur. Prod. Chem. (2005), 30, 797-823 (27 pgs).
Comer, S. D., Sullivan, M. A,; Hulse, G. K., Sustained-release naltrexone: novel treatment for opioid dependence, Exp. Opin. Invest. Drugs, (2007), 16(8), 1285-1294 (11 pgs).
Cunningham, C.W., Coop, A.,Therapeutic applications of opioid antagonists, Chimica Oggi, 24(3), 54-57 (2006) (5 pgs).
Eguchi, M., Recent advances in selective opioid receptor agonists and antagonists, Med. Res. Rev., (2004), 24(2),182-212 (31 pgs).
Furst, S., Hosztafi, S., Friedmann, T., Structure-Activity Relationships of Synthetic and Semisynthetic Opioid Agonists and Antagonists, Curr. Med. Chem., (1995), 1, 423-440 (20 pgs).
Goodman, A. J.; Le Bourdonnec, B.; Dolle, R. E. Mu opioid receptor antagonists: recent developments, ChemMedChem (2007), 2(11), 1552-1570 (22 pgs).
Heidbreder, C., Novel pharmacotherapeutic targets for the management of drug addiction, Eur. J. Pharmacol., (2005), 526 (1-3), 101-112 (12 pgs).
Hemy, B.; Brotchie, J. M., Potential of opioid antagonists in the treatment of levodopa-induced dyskinesias in Parkinson's disease (A review and discussion), Drugs & Aging (1996), 9(3), 149-158 (11 pgs).

(Continued)

*Primary Examiner* — Celia Chang
(74) *Attorney, Agent, or Firm* — Don D. Cha; Hamilton DeSanctis & Cha, LLP

(57) ABSTRACT

The invention provides compounds that bind with high affinities to the μ-, δ- and κ-opioid receptors and α$_2$-adrenoreceptor. In addition to providing these compounds with novel pharmacological binding properties, the invention also describes detailed novel methods for the preparation of representative compounds and a scheme for the synthesis of related compounds that bind to the opioid receptors and/or α$_2$-adrenoreceptor.

11 Claims, 1 Drawing Sheet

(56) References Cited

OTHER PUBLICATIONS

Hipkin, R. W.; Dolle, Roland E., Opioid receptor antagonists for gastrointestinal dysfunction, Ann. Rep. Med. Chem., (2010), 45, 143-155 (15 pgs).

Husbands, S.M., Lewis, J.W., Opioid ligands having delayed long-term antagonist activity: Potential pharmacotherapies for opioid abuse, Mini-Revi. Med. Chem., (2003), 3(2), 137-144 (9 pgs).

Kaczor, A., Matosiuk, D., Non-peptide opioid receptor ligands—recent advances. Part II. Antagonists, Curr. Med. Chem., (2002), 9(17), 1591-1603 (13 pgs).

Krishnan-Sarin, S., O'Malley, S.S., Opioid antagonists for the treatment of nicotine dependence, Med. Treat. Nicotine Depend., (2007) 123-135 (9 pgs).

Lauretti, G.R., Highlights in opioid agonists and antagonists, Expert Rev. Neurotherapeut., 6(4), 613-622 (2006) (15 pgs).

Leslie, J. B., Alvimopan: a peripherally acting Mu-. Opioid receptor antagonists, Drugs of Today (2007), 43(9), 611-625 (9 pgs).

Lewitt P. A; Hauser R. A; Lu M.; Nicholas A. P.; Weiner W.; Coppard N.; Leinonen M.; Savola J.-M., Randomized clinical trial of fipamezole for dyskinesia in Parkinson disease (FJORD study), Neurology (2012), 79(2), 163-169 (7 pgs).

Lowengrub, K., Iancu, I., Aizer, A., Kotler, M., Dannon, P.N., Pharmacotherapy of pathological gambling: review of new treatment modalities, Exp. Rev. Neurotherapeut., (2006), 6(12), 1845-1851 (13 pgs).

Metcalf, M. D., Coop A., Kappa opioid antagonists : past successes and future prospects, The AAPS J., (2005), 7(3), E704-E722 (19 pgs).

Millan M. J., From the cell to the clinic: a comparative review of the partial D2/D3 receptor agonist and a2-adrenoreceptor antagonists, piribedil, in the treatment of Parkinson's disease Pharmacol. Therapeut. (2010), 128(2), 229-273 (45 pgs).

Portoghese, P. S., Bivalent ligands and the message-address concept in the design of selective opioid receptor antagonists, Trends Pharm. Sci., (1989), 10(6), 230-235 (6 pgs).

Portoghese, P. S., Selective nonpeptide opioid antagonists, Handbook of Experimental Pharmacology, (1993), 104/1(Opioids I), 279-293 (15 pgs).

Portoghese, P. S., The design of delta-selective opioid receptor antagonists, Farmaco, (1993), 48(2), 243-251 (10 pgs).

Raisch, D.W., Fye, C. L., Boardman, K. D., Sather, M. R. Opioid dependence treatment, including buprenorphine/naloxone. Annals Pharmacother (2002), 36(2), 312-321 (10 pgs).

Roozen, H. G., de Waart, R., van der Windt, D. A. W. M., van den Brink, W., de Jong, C. A. J., Kerkhof, A. J. F. M., A systematic review of the effectiveness of naltrexone in the maintenance treatment of opioid and alcohol dependence, Eur. Neuropsychopharmacol., (2006), 16(5), 311-323 (13 pgs).

Schmidhammer, H., Opioid receptor antagonists, Prog. Med. Chem., (1998), 35, 83-132 (50 pgs).

Soyka, M.; Roesner, S., Opioid antagonists for pharmacological treatment of alcohol dependence—a critical review, Curr. Drug Abuse Rev., (2008), 1(3), 280-291 (13 pgs).

Stotts, A. L.; Dodrill, C. L.; Kosten, T. R. Opioid dependence treatment: options in pharmacotherapy, Exp. Opin. Pharmacother., (2009), 10(11), 1727-1740 (21 pgs).

Takemori, A. E., Portoghese P S Selective naltrexone-derived opioid receptor antagonists, Ann. Rev. Pharm. Tox., (1992), 32, 239-269 (31 pgs).

Taylor, R., Jr.; Pergolizzi, J. V., Jr.; Porreca, F.; Raffa, R. B. Opioid antagonists for pain Exp. Opin. Invest. Drugs, (2013), 22(4), 517-525 (10 pgs).

Thayer, A., Drugs to Fight Addictions, Chem. Eng. News, (2006), 84(39), 21-44 (24 pgs).

van Dorp, E. L. A., Yassen, A., Dahan, A., Naloxone treatment in opioid addiction: the risks and benefits, Exp. Opin. Drug Safety, (2007), 6(2), 125-132 (10 pgs).

White, J.M., Lopatko, O.V., Opioid maintenance: a comparative review of pharmacological strategies, Expert Opin. Pharmacotherapy, (2007), 8(1), 1-11 (12 pgs).

Woods, J.H., Traynor, J.R., Evaluation of new compounds for opioid activity (2000), NIDA Research Monograph, Volume Date 2000, 181 (Problems of Drug Dependence 2000), (2001), 140-155 (47 pgs).

Yuan, C.-S., Israel, R. J., Methylnaltrexone, a novel peripheral opioid receptor antagonist for the treatment of opioid side effects, Exp. Opin. Invest. Drugs, (2006), 15(5), 541-552 (13 pgs).

Zimmerman, D. M., Leander, J. D., Opioid antagonists: structure activity relationships, NIDA Research Monograph, (1990), 96, 50-60 (1990) (12 pgs).

Pubchem. Substance Record for SID 56006844. Deposit Date: Oct. 8, 2008. Retrieved on Nov. 11, 2015. Retrieved from the Internet. <URL: http://pubchem.ncbl.nlm.nlh.gov/substance/56006844#section=Top>. Entire document.

Pubchem. Substance Record for SID 150462038. Deposit Date: Oct. 23, 2012. [retrieved on Nov. 10, 2015]. Retrieved from the Internet. <URL: https://pubchem.ncbi.nlm.nih.gov/substance/150462038/version/1>.entire document.

* cited by examiner

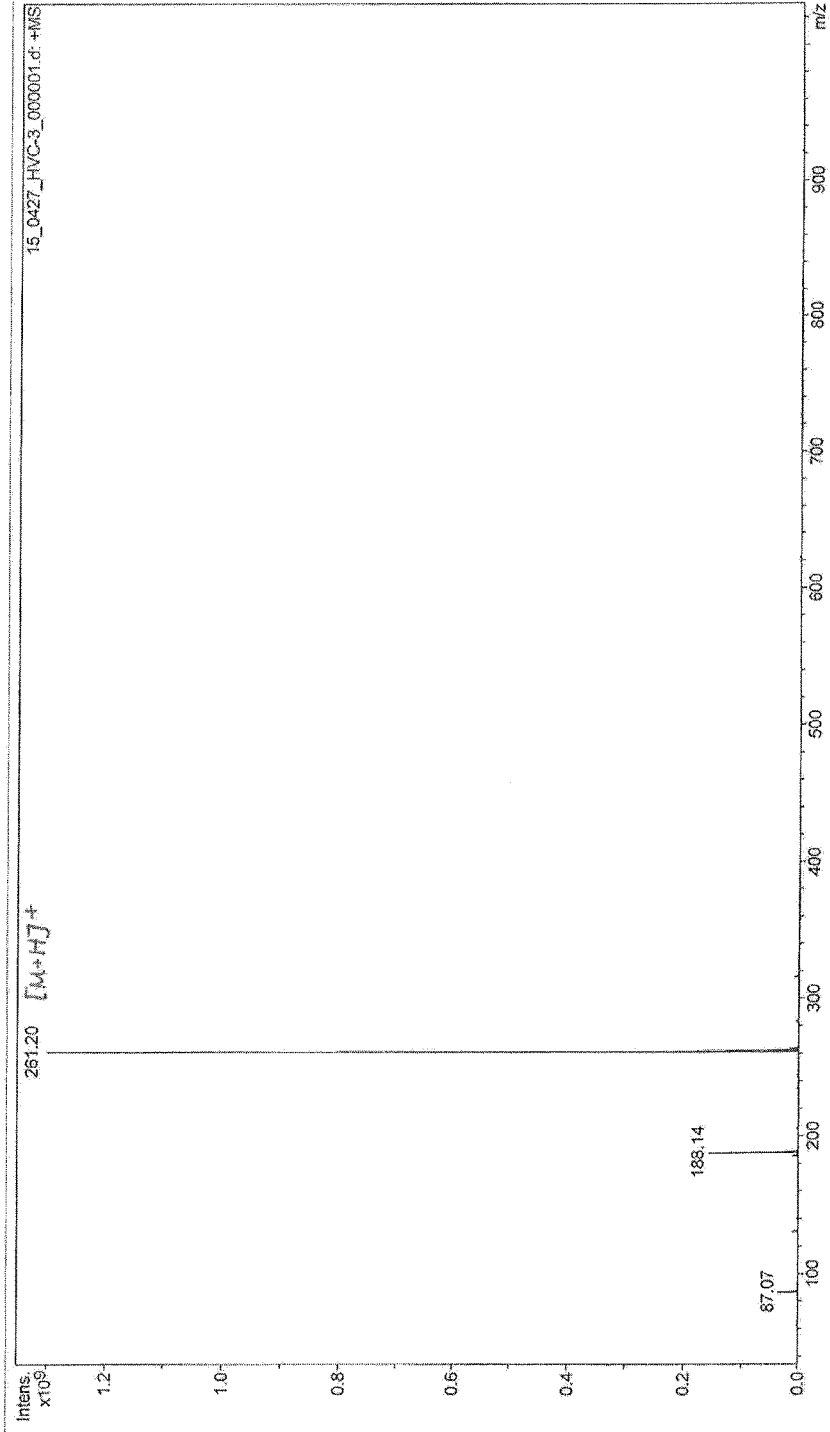

SUBSTITUTED 1-ARYLETHYL-4-ACYLAMINOPIPERIDINE DERIVATIVES AS OPIOID/ALPHA-ADRENORECEPTOR MODULATORS AND METHOD OF THEIR PREPARATION

CROSS REFERENCE TO RELATED APPLICATION

This application claims priority from U.S. Provisional Application Ser. No. 62/040,886, filed Aug. 22, 2014, the contents of which are incorporated herein by reference.

STATEMENT REGARDING FEDERALLY SPONSORED RESEARCH OR DEVELOPMENT

This invention was made with government support under Grant No. R01 DK017420, R01 GM108040, and P01 DA006284, awarded by NIH. The government has certain rights in the invention.

FIELD OF THE INVENTION

The invention relates to novel pharmacological compounds, and more specifically to the creation of a new class of small molecules which simultaneously exhibit high binding affinities to the μ-, δ-, and κ-opioid receptors and the $\alpha_2$-adrenoreceptor. The binding activity is believed to be antagonistic at least with respect to the μ-opioid receptors. In addition to providing these compounds with novel pharmacological binding properties, the invention also describes detailed novel methods for the preparation of representative compounds and a scheme for the synthesis of related compounds that bind to the opioid receptors and/or $\alpha_2$-adrenoreceptor.

BACKGROUND OF THE INVENTION

Opioid antagonists are drugs which bind to the opioid receptors with higher affinity than opioid agonists but do not activate the opioid receptors. Commonly known opioid antagonists include drugs such as, for example, naltrexone, naloxone, nelmefene, nalorphine, and nalbuphine. Opioid antagonists effectively block the receptor from the action of both naturally occurring agonists (e.g., morphine, codeine, thebaine) and synthetic agonists (e.g., fentanyl, pethidine, levorphanol, methadone, tramadol, dextropropoxyphene) and uses include counteracting life-threatening depression of the central nervous and respiratory systems and thus are used for emergency overdose and dependence treatment (e.g., naloxone). There are many excellent reviews dedicated to different aspects of opioid antagonists [28-46].

Opioid receptor antagonists are known to modulate numerous central and peripheral effects including those associated with opioid abuse, the development of opioid tolerance and dependence, opioid-induced constipation, alcohol and cocaine abuse, depression, and immune responses [1]. The diverse therapeutic applications of μ-opioid antagonists include opioid-overdose-induced respiratory depression, opioid and cocaine abuse, alcohol dependence, smoking cessation, obesity, psychosis[1-19] and for the treatment of dyskinesia associated with Parkinson's disease [20-27].

The few opioid antagonists, currently on the market are represented by very few drugs (e.g., naloxone, naltrexone, and nalorphine (a partial agonist)) that have been shown to have therapeutic utility in a variety of indications. During last two decades only Alvimopan [13,14]—a peripherally acting μ-opioid antagonist for the treatment of postoperative ileus—has received approval as new drug. In addition, some azabicyclohexane derivatives and series of bi(hetero)aryl ethers as biological tools have been proposed as new chemical entities in this class of compounds [15].

Every chemical class of compounds with opioid-agonist activity has a structurally similar opioid-antagonist pair. Agonist-antagonist transformation in any of these cases takes place as a result of a small change in the structure of the agonist. The only exceptions, where the corresponding change for agonist-antagonist transformations has not been found, are the compounds of the fentanyl series.

Since the discovery of the "army" of opioid agonists of the fentanyl series (sufentanyl, alfentanyl, carfentanyl, remifentanyl, etc.) beginning in the 1960s, a structurally corresponding antagonist has not been found for any of these compounds. Thus, for decades there has been an evident gap in the art with respect to a possible specific structural change that could make possible the transformation of powerful opioid agonist properties of compounds of fentanyl series into powerful antagonists.

Similar to the general action of the opioid antagonists, antagonists of the adrenoreceptors (adrenergic receptors) bind to the adrenoreceptors and act to inhibit the action of those receptors. Alpha antagonists, or alpha-blockers, may selectively act at the $\alpha_1$-adrenoreceptors or at the $\alpha_2$-adrenoreceptors, or they may non-selectively act at both receptors. Commonly known α-blockers include, for example, phenoxybenzamine and phentolamine (non-selective); alfuzosin and prazosin ($\alpha_1$-blockers); and atipamezole, idazoxan, mirtazapine and yohimbine ($\alpha_2$-blockers). Generally, α-blockers have shown to be effective in the treatment of various medical conditions, including Raynaud's disease, hypertension, scleroderma, anxiety and panic disorders, and in the treatment of dyskinesia associated with Parkinson's disease.

SUMMARY OF THE INVENTION

The present invention is based on the discovery of certain compounds exhibiting high binding affinity for the μ-, δ-, and κ-opioid receptors and the $\alpha_2$-adrenoreceptor. The compounds are believed to exhibit antagonistic activity at least with respect to μ-opioid receptors. The compounds are structurally related to the fentanyl series of opioid receptor agonists. Processes for preparing these compounds are also included in this disclosure.

In one embodiment of the disclosure, a compound having the formula

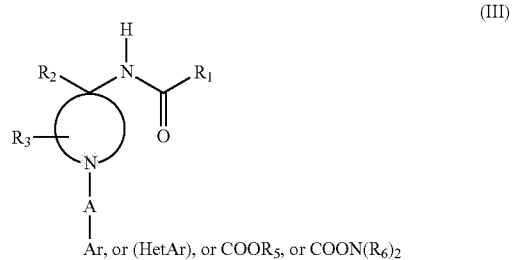

is disclosed, wherein $R_1$ is H, substituted or unsubstituted $C_1$-$C_{10}$ alkyl, alkenyl, or alkynyl, or substituted or unsubstituted aryl or hetaryl; $R_2$ is H, —$CH_2O$—$C_{1-4}$ alkyl; COO—$C_{1-4}$ alkyl; —$CONR_4$; $R_3$ is H, substituted or unsubstituted $C_1$-$C_{10}$ alkyl, alkylene, alkynyl, or substituted or unsubstituted aryl or hetaryl; A is substituted or unsubstituted $C_1$-$C_{10}$ alkyl, alkylene, alkynyl; Ar or HetAr is substituted or unsubstituted monocyclic or polycyclic aromatic or heteroaromatic moiety; $COOR_5$, or $CON(R_6)_2$, where $R_5$ and $R_6$ are H, substituted or unsubstituted $C_1$-$C_{10}$ alkyl, alkylene, alkynyl, or substituted or unsubstituted aryl or hetaryl; the central nitrogen-containing ring is a substituted or unsubstituted 5- to 7-membered heterocyclic ring; and pharmaceutically acceptable salts of said compound.

In a preferred embodiment, the prepared compound may belong to the series of N-(1-arylethylpiperidin-4-yl)acylamides. In another embodiment, the compound may be N-(1-phenethylpiperidin-4-yl)propionamide (Compound I, below). In yet another embodiment the compound may be the oxalate salt, or other pharmaceutically acceptable salt, of N-(1-phenethylpiperidin-4-yl)propionamide.

In another embodiment, a process for preparing a compound of formula III is provided. The process comprising the following steps: (a) reacting a cyclic ketone having a protecting group in a Grignard or Reformatsky reaction to obtain a first product; (b) reacting the product of step (a) in a Ritter reaction to obtain a second product; and (c) deprotecting the product of step (b) with acylation or alkylation to obtain a compound of formula III.

In yet another embodiment, a process for preparing a compound of formula III is provided, comprising the following steps: (a) reacting a cyclic ketone having a protecting group in a Strecker reaction to obtain a first product; (b) reacting the product of step (a) in a selective carbalkoxy group transformation to obtain a second product; and (c) deprotecting the product of step (b) with acylation or alkylation to obtain a compound of formula III.

In another embodiment, a process for preparing N-(1-phenethylpiperidin-4-yl) propionamide is provided, comprising the following steps: (a) reacting phenethylpiperidin-4-one with hydroxylamine hydrochloride in ethanol in the presence of a base, to produce 1-phenethylpiperidin-4-one oxime; (b) reducing the oxime obtained in step (a) with iso-amyl alcohol and sodium metal to produce 1-phenethylpiperidin-4-amine; and (c) acylating the product of step (b) with propionic acid chloride in chloroform in the presence of triethylamine to produce N-(1-phenethylpiperidin-4-yl)propionamide. The N-(1-phenethylpiperidin-4-yl)propionamide may optionally be further treated with oxalic acid to obtain N-(1-phenethylpiperidin-4-yl)propionamide oxalate.

BRIEF DESCRIPTION OF THE DRAWINGS

These and other embodiments, features and advantages of the present invention will become more fully apparent when read in conjunction with the following detailed description taken in conjunction with the accompanying drawings, wherein FIG. 1 is a (LC/MS) plot of a preferred compound designated HVC-3.

DETAILED DESCRIPTION OF THE INVENTION

For the purposes of this disclosure, a "salt" is any acid addition salt, preferably a pharmaceutically acceptable acid addition salt, including but not limited to, halogenic acid salts such as hydrobromic, hydrochloric, hydrofluoric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethan sulfonic, ethanesulfonic, benzenesulfonic or p-toluenesulfonic), acetic, malic, fumaric, succinic, citric, benzoic, gluconic, lactic, mandelic, mucic, pamoic, pantothenic, oxalic and maleic acid salts; and an amino acid salt such as aspartic or glutamic acid salt. The acid addition salt may be a mono- or di-acid addition salt, such as a di-hydrohalogenic, di-sulfuric, di-phosphoric or di-organic acid salt. In all cases, the acid addition salt is used as an achiral reagent which is not selected on the basis of any expected or known preference for interaction with or precipitation of a specific optical isomer of the products of this disclosure.

"Pharmaceutically acceptable salt" is meant to indicate those salts which are, within the scope of sound medical judgment, suitable for use in contact with the tissues of a patient without undue toxicity, irritation, allergic response and the like, and are commensurate with a reasonable benefit/risk ratio. Pharmaceutically acceptable salts are well known in the art. For example, Berge et al. (1977) J. Pharm. Sciences, vol. 6. 1-19, which is hereby incorporated by reference in its entirety, describes pharmaceutically acceptable salts in detail.

"Modulation" is meant to refer to the binding activity of a compound with respect to a particular receptor. The binding activity of the compound, or "modulator," may be that of an agonist, inverse agonist, antagonist, allosteric regulator, positive allosteric modulator, negative allosteric modulator, or any other type of ligand-receptor interaction that is known in the art.

In this invention we disclose a new class of molecules that simultaneously bind with high affinity to opioid μ-, δ-, κ-receptors and also to α-adrenoreceptors, thereby exhibiting modulation-type interactions with those receptors. The interaction of the molecules with μ-receptors is believed to have the character of antagonist action, based at least in part on the observed high affinity binding of the molecules with respect to the μ-receptors.

Although not wishing to be bound by theory, it appears that the principal structural change for agonist-antagonist transformation is the removal of a phenyl group from an N-phenylpropionamide fragment of fentanyl. This transformation is depicted below, wherein N-(1-phenethylpiperidin-4-yl)-N-phenylpropionamide (II) is transformed to N-(1-phenethylpiperidin-4-yl)-N-propionamide (I), causing a transformation of μ-agonist properties to μ-antagonist with simultaneous modulation of delta-, kappa- and alpha-receptors:

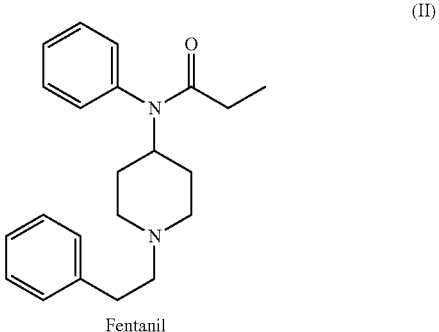

Fentanil (II)

-continued

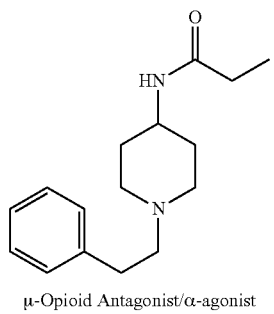

µ-Opioid Antagonist/α-agonist

The invention also relates to processes for preparing compounds of general formula III, which are pharmacologically active compounds:

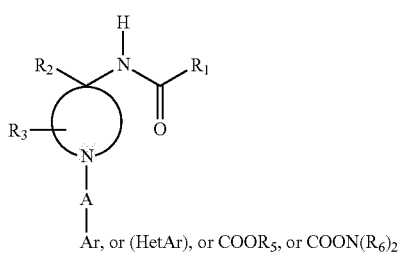

Representative compounds of the present invention also include the following compounds, wherein the central nitrogen containing ring is a substituted or unsubstituted 5- to 7-membered heterocyclic ring:

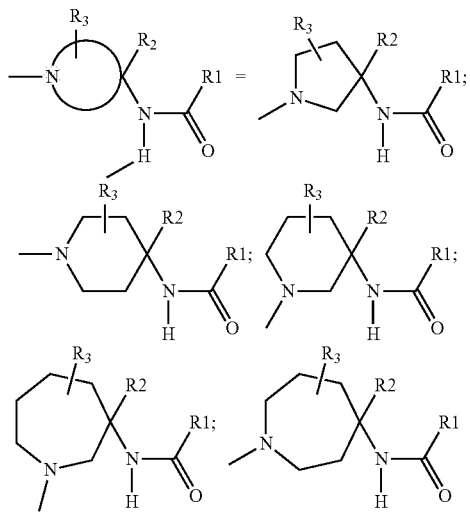

These compounds may include the following structural and functional groups:

$R_1$ is H, substituted or unsubstituted $C_1$-$C_{10}$ alkyl, alkenyl, alkynyl, or substituted or unsubstituted aryl or hetaryl;

$R_2$ is H, —$CH_2O$—$C_{1-4}$ alkyl, etc.; COO—$C_{1-4}$ alkyl, etc.; —$CONR_4$ etc.;

$R_3$ is H, substituted or unsubstituted $C_1$-$C_{10}$ alkyl, alkylene, alkynyl, or substituted or unsubstituted aryl or hetaryl;

A is substituted or un-substituted $C_1$-$C_{10}$ alkyl, alkylene, alkynyl;

Ar or HetAr is substituted or un-substituted monocyclic or polycyclic aromatic or heteroaromatic moiety; and $COOR_5$, or $CON(R_6)_2$, where $R_5$ and $R_6$ are H, substituted or unsubstituted $C_1$-$C_{10}$ alkyl, alkylene, alkynyl, or substituted or un-substituted aryl or hetaryl.

In certain embodiments of the invention, compounds of formula (III) can be prepared according to the following general schemes (wherein PG is a protecting group):

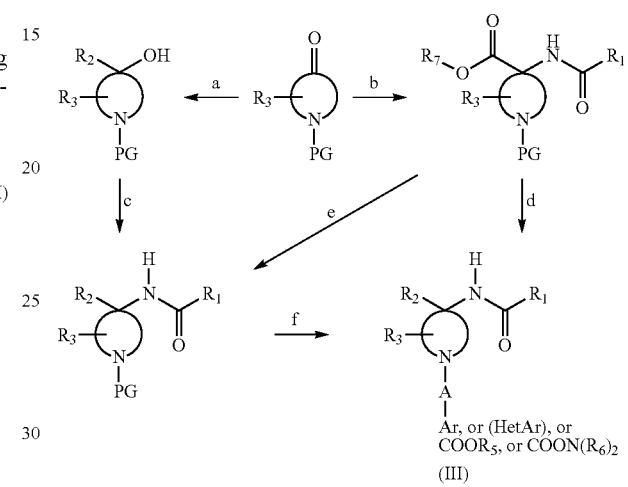

As shown above, these schemes generally include transformations of different starting cyclic ketones (e.g., a variety of piperidin-4-ones, pyrrolidin-3-ones and azepan-4-one) to desired compounds of formula (III) via, for example:

a) Grignard or Reformatsky type reactions;
b) a Strecker type reaction;
c) a Ritter type reaction;
d) selective carbalkoxy group transformations, deprotection, and further appropriate acylation or alkylation;
e) selective carbalkoxy group transformations; or
f) deprotection with further appropriate acylation or alkylation.

The process for the preparation of the first example of µ-opioid modulator/α-modulator N-(1-phenethylpiperidin-4-yl)propionamide and its salt is described in the present invention in detail below (Scheme 1):

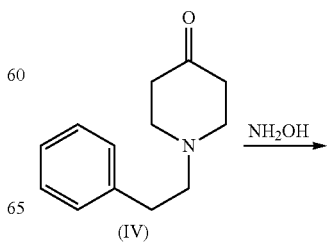

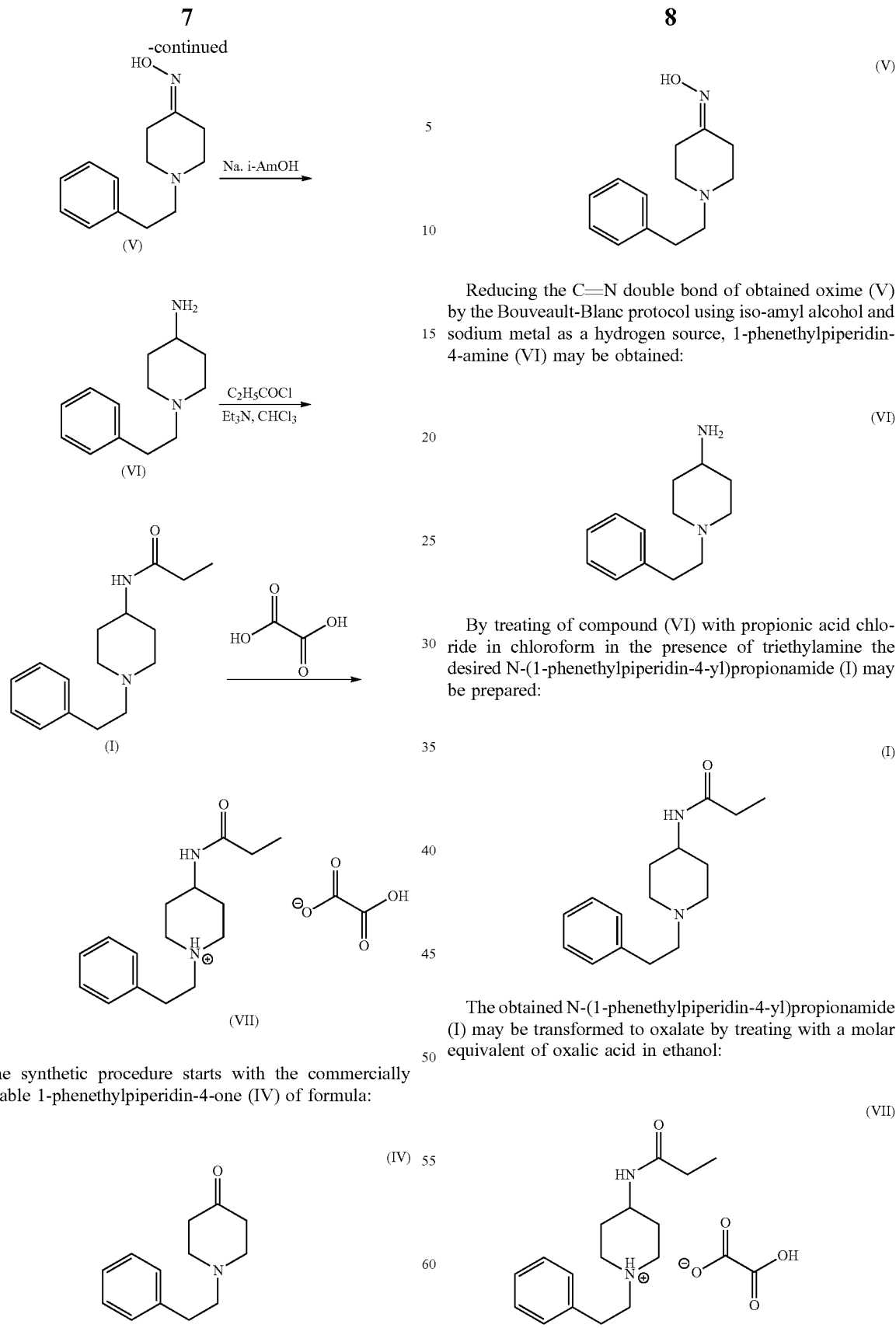

Reducing the C=N double bond of obtained oxime (V) by the Bouveault-Blanc protocol using iso-amyl alcohol and sodium metal as a hydrogen source, 1-phenethylpiperidin-4-amine (VI) may be obtained:

By treating of compound (VI) with propionic acid chloride in chloroform in the presence of triethylamine the desired N-(1-phenethylpiperidin-4-yl)propionamide (I) may be prepared:

The obtained N-(1-phenethylpiperidin-4-yl)propionamide (I) may be transformed to oxalate by treating with a molar equivalent of oxalic acid in ethanol:

The synthetic procedure starts with the commercially available 1-phenethylpiperidin-4-one (IV) of formula:

which may be reacted with hydroxylamine hydrochloride in ethanol in the presence of base, to give 1-phenethylpiperidin-4-one oxime (V) of formula:

The tables (Tables 1-3) in the attached Appendix 1 incorporated herein by reference include data from binding assays performed with the N-(1-phenethylpiperidin-4-yl)propionamide compound (I). This data demonstrates the high binding affinities of the compounds of the invention for μ-, δ-, and κ-opioid receptors and for α2-adreno-receptors. Table 1 illustrates the results of binding assays performed with the N-(1-phenethylpiperidin-4-yl)propionamide (compounds R1 and R2) and various receptors. As can be seen in the table, at a test concentration of 1.0E-05 M, N-(1-phenethylpiperidin-4-yl)propionamide demonstrated the highest percentage binding inhibition of control specific binding with respect to the α2B adrenoreceptor (74% and 55%); the δ-opioid receptor (44% and 69%); the κ-opioid receptor (107% and 104%); the μ-opioid receptor (98% and 99%). Table 2 contains reference compound data for the various receptors used in the binding assays. Finally, Table 3 provides summary results of the binding assays, showing the receptors from Table 1 for which the test compound demonstrated the highest percentage binding inhibition of control specific binding.

Appendix 2 incorporated herein by reference includes x-ray crystallography data for a representative compound of the invention, N-(1-phenethylpiperidin-4-yl)propionamide oxalate.

Appendix 3 incorporated herein by reference includes data showing that a representative compound of the invention, N-(1-phenethylpiperidin-4-yl)propionamide, conforms to "Lipinski's rule of five," which provides a general rule of thumb for evaluating the activity of an orally administered drug.

The compounds of the present invention may be utilized in various pharmaceutical and medical applications in which the use of a compound exhibiting high binding affinities for μ-, δ- or κ-opioid receptors and/or α2-adreno-receptors is indicated. The compounds may be of particular use in applications in which the use of a μ-, δ- or κ-opioid receptor modulator, including particularly a μ-opioid receptor antagonist, and/or an α2-adrenoreceptor modulator is indicated. Accordingly, in certain embodiments, the present invention also includes salts, and particularly pharmaceutically acceptable salts, of the disclosed compounds, as well as processes for preparing the salt forms of the disclosed compounds.

EXAMPLES

The following examples illustrate the preparation of N-(1-phenethylpiperidin-4-yl)propionamide and its oxalate salt form, N-(1-phenethylpiperidin-4-yl)propionamide oxalate, in accordance with the present disclosure.

Example 1

1-Phenethylpiperidin-4-one oxime (Compound V)

1-Phenethylpiperidin-4-one (10.15 g (0.05 mol) dissolved in 60 mL of ethanol) was added drop-wise at 0° C. to a solution of hydroxylamine in water. The water solution of hydroxylamine was preliminarily prepared by adding at 0° C. in portions 13.8 g (0.1 mol) of $K_2CO_3$ to the solution of 6.95 g (0.1 mol) hydroxylamine hydrochloride in 50 mL of water. The mixture was set aside for a night. Ethanol was evaporated under slight vacuum. Water (~100 mL) was added, and the mixture was stirred on ice bath for an hour. The separated solid product was filtered, washed with water and allowed to air-dry. The crude oxime (10.71 g (98.25%), m.p. 132-134° C.) was reserved for use in the next reaction without further purification. Analysis with electrospray ionization mass spectrometry (MS (ESI)) resulted in a peak at 219.1 (MH+).

Example 2

1-Phenethylpiperidin-4-amine (Compound VI)

1-Phenethylpiperidin-4-one oxime (6.54 g (0.03 mol)) was dissolved in 100 mL of dry i-AmOH on heating. A ten-fold excess of sodium (6.9 g (0.3 mol)) was slowly (1 hour) added to the stirred solution in small pieces, while the temperature was maintained around 110°. The solution was stirred on heating at 110° for two hours and left to cool to room temperature. 150 mL of ether, followed by 75 mL of water, was then added to the solution. The organic layer was separated and dried on $MgSO_4$. After evaporation of solvents under slight vacuum, the product was distilled to give 4.3 g (70%) of 1-phenethylpiperidin-4-amine (VI) with a boiling point of 138-142°/1.5 mm. MS (ESI): 205.0 (MH+).

Example 3

N-(1-Phenethylpiperidin-4-yl)propionamide (Compound I)

Propionyl chloride (2.775 g (0.03 mol)) in 5.55 mL of $CHCl_3$ was added drop-wise on stirring to the cooled (0° C.) solution of 4.08 g (0.02 mol) 1-phenethylpiperidin-4-amine and 3.03 g (0.03 mol) of $Et_3N$ in 30 mL of $CHCl_3$. The mixture was left to come to room temperature and stirred overnight. After working up with 5% solution of $NaHCO_3$ (2.52 g (0.03 mol)) in 47.88 $H_2O$, the organic layer was separated, washed with water and dried on $MgSO_4$. After evaporation of solvents under slight vacuum, the residue was crystallized from hexane to give 4.9 g (94%) of N-(1-phenethylpiperidin-4-yl)propionamide (I) with m.p. 134-135°. MS (ESI): 261.2 (MH+).

The results of proton NMR spectroscopy were as follows:
$^1$H NMR (600 MHz, $CDCl_3$): δ 7.27 (t, J=7.4 Hz, 2H), 7.19 (m, 3H), 5.32 (d, J=7.4 Hz, 1H), 3.82 (qt, J=7.8, 4.2 Hz, 1H), 2.92 (dt, J=11.8, 3.4 Hz, 2H), 2.79 (m*, 2H), 2.59 (m*, 2H), 2.19 (q, J=7.5 Hz, 2H), 2.18 (m, 2H), 1.95 (dtd, J=12.4, 4.4, 1.7 Hz, 2H), 1.46 (qd, J=11.7, 3.8 Hz, 2H), 1.15 (t, J=7.5 Hz, 3H).

* these two multiplets arise from two methylene groups that have magnetically inequivalent protons AA'BB' with $^2J_{AA'}=^2J_{BB'}$,12 Hz, $^3J_{AB}=3J_{A'B'}$=11 Hz, $^3J_{AB'}=^3J_{A'B}$=4 Hz, consistent with a preferred anti conformation for the phenyl and piperidine rings The results of carbon-13 NMR spectroscopy were as follows:
$^{13}$C NMR (150 MHz, $CDCl_3$): δ 173.0, 140.2, 128.6, 128.4, 126.0, 60.4, 52.3, 46.3, 33.7, 32.3, 29.8, 9.9.

Example 4

N-(1-Phenethylpiperidin-4-yl)propionamide oxalate (Compound VII)

Oxalic acid (1 g (0.011 mol)) in 10 mL of ethanol was added drop-wise to the solution of 2.93 g (0.011 mol) of N-(1-phenethylpiperidin-4-yl)propionamide (I) in 29.3 mL of ethanol. The mixture was set aside overnight. The obtained crystals were then separated and dried in a desiccator over P₂O₅ to give 3.5 g of N-(1-phenethylpiperidin-4-yl)propionamide oxalate (VII) with m.p. 216-218 (MS (ESI): 261.2 ([M+H])—see FIG. 1

The compound designated as HCV-3 was then subject to cellular functional assay and results reported below:

taken at 0, 5, 15, 30 and 45 minutes and quenched immediately. The samples were extracted and analyzed by LC-MS/MS. Compound HCV-3 was observed to have low clearance in human, monkey and mouse microsomes, and moderate clearance in rat.

| Cellular functional assays | | | | | | | |
|---|---|---|---|---|---|---|---|
| Experimental Assay | Catalog Ref Client Com Batch | Compound Test Conce % of Contro % of Agonist Response | | $1^{st}$ | $2^{nd}$ | Mean | Reference $EC_{50}$ Ref (M) |
| 27/07/201α 2B (h 1813 | HCV-3 1 | 1000233221.0E−05 | 7.1 | 9.2 | 5.1 | 7.1 | dexmedete 1.3E−08 |
| 27/07/200 κ (KO 2071 | HCV-3 1 | 1000233221.0E−05 | −4.2 | −10.3 | 1.8 | −4.2 | U 50488 1.6E−09 |
| 27/07/201 μ (MOP) 1392 | HCV-3 1 | 1000233221.0E−05 | 33.5 | 28.1 | 38.9 | 33.5 | DAMGO 4.2E−09 |
| Experimental Assay | Catalog Ref Client Com Batch | Compound Test Conce % Inhibition Agonist Response (% of Control) | | $1^{st}$ | $2^{nd}$ | Mean | Reference IC50 Ref(N KbRef (M) |
| 27/07/201 α2B(h 1814 | HCV-3 1 | 1000233221.0E−05 | −28 | 116.8 | 138.7 | 127.8 | yohimine 3.7E−07 4.8E−08 |
| 27/07/201 κ (KO 2072 | HCV-3 1 | 1000233221.0E−05 | 6 | 112.4 | 76.5 | 94.4 | nor-BNI 4.3E−10 7.2E−11 |
| 27/07/201 μ (MOP) 1393 | HCV-3 1 | 1000233221.0E−05 | −1 | 100.1 | 101.8 | 101.0 | CTOP 2.1E−07 2.3E−08 |

Compound HCV-3 also was tested for hERG inhibition. Over the concentration range tested (up to 25 micromolar) no dose-response was obtained. Therefore the inhibition $IC_{50}$ was considered as >25 micromolar. There was a hint of some inhibition at the top concentration of 25 micromolar, with 32.5% inhibition observed (insufficient to generate an $IC_{50}$ value). As such, this compound is categorised as having weak or no hERG inhibition. The control compounds behaved as expected in the assay.

Compound HCV-3 also was tested for CYP inhibition, and was found to inhibit CYP2D6, and to weakly inhibit CYP2C19. However, with CYP2C19 the inhibition was too weak to generate an $IC_{50}$ value, and we observed just 36.4% inhibition at the top concentration of 25 micromolar. With CYP2D6, an $IC_{50}$ of 4.2 micromolar was observed. Thus, this compound was considered to be a moderate CYP2D6 inhibitor, and a weak CYP2C19 inhibitor. No inhibition was observed at CYP2B6, CYP2C9, CYP3A4 (with either substrate), CYP2C8 or CYP1A2. The significance of this CYP2D6 inhibition will depend on the levels of the compound in vivo.

Compound HCV-3 also was tested in cellular and nuclear receptor functional assays, and the results reported in Appendix 4, incorporated herein by reference.

Compound HCV-3 was also subjected to AMES testing, and the results reported in Appendix 5, incorporated herein by reference.

In summary, the compound HCV-3 was negative for genotoxicity against both strains used in this assay (TA98 and TA 100) up to a maximum tested concentration of 1 mg/mL, in both the absence and presence of S9 metabolic activation. The assay controls behaved as expected.

Compound HCV-3 also was subjected to in vitro metabolic disposition in mouse, rat, monkey and human microsomes. The test compound was incubated with pooled liver microsomes, since drip stability in liver microsomes can be predictive of drug stability in vivo. Aliquots were Compound HCV-3 also was subjected to MDCK permeability assay. The compound was observed to be highly permeable in the MDCK assay. There was a slight difference between the plus and minus inhibitor data in terms of the efflux ratio obtained (1.48 minus inhibitor, versus 0.929 plus inhibitor). A ratio of greater than 2 generally indicates that efflux, i.e., blood brain barrier permeability, is occurring. The control compounds behaved as expected, with prazosin (a P-gp substrate) showing efflux in the absence of Cyclosporin A, which was inhibited in its presence.

Various derivatives of the above compounds with potential opiod and alpha antagonist activity were prepared as follows, and characterized by NMR and mass-spec as reported below.

Protocols for the synthesis of substituted 1-arylethyl-4-acylaminopiperidine derivatives Synthesis of 1-benzylpiperidin-4-one oxime

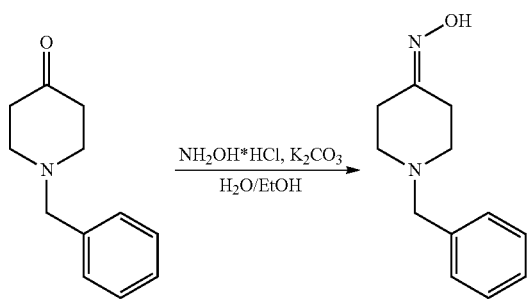 [SMILES: O=C1CCN(Cc2ccccc2)CC1 ; "NH2OH*HCl, K2CO3" ; ON=C1CCN(Cc2ccccc2)CC1]

28.35 g (1 equiv., 0.15 mol) of 1-benzylpiperidin-4-one was dissolved in 60 mL of EtOH and then cooled to 0° C. using an ice bath. A solution containing 20.85 g (2 equiv., 0.30 mol) of hydroxylamine hydrochloride dissolved in 75 mL of H₂O was prepared and then added dropwise to the reaction mixture followed by dropwise addition of a solution containing 20.7 g (1 equiv., 0.15 mol) of K₂CO₃ dissolved in 75 mL of H₂O. The reaction mixture was then brought to room temperature and stirred overnight. The EtOH was then removed via rotary evaporation and the reaction mixture was then cooled in an ice bath to allow the product to crystallize out of solution. The product was filtered and washed several times with H₂O and recrystallized in EtOH. Yield: 27.78 g (70.17%).

Synthesis of 1-benzylpiperidin-4-amine

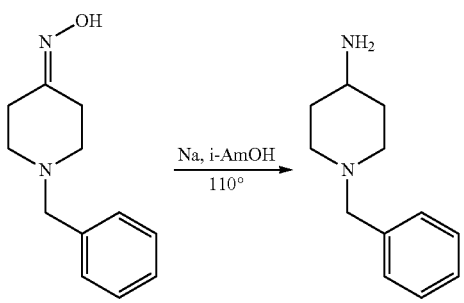 [SMILES: ON=C1CCN(Cc2ccccc2)CC1 ; NC1CCN(Cc2ccccc2)CC1]

A solution containing 6.12 g (1 equiv., 0.03 mol) of 1-benzylpiperidin-4-one oxime dissolved in 90 mL of iso-amyl alcohol was prepared and heated to approximately 110° C. 6.9 g (10 equiv., 0.3 mol) of Na metal was then added slowly to the reaction mixture. After addition of Na, the reaction mixture was allowed to cool to room temperature and stirred until the reaction mixture turned into a thick slurry. The slurry was dissolved in 50 mL of ethyl acetate and 25 mL of H₂O. The organic layer was separated and washed with H₂O (2×20 mL) followed by drying over anhydrous magnesium sulfate. The solvent was removed via rotary evaporation, resulting in a yellow oil. The crude product was purified via column chromatography utilizing silica gel and a DCM:MeOH solvent system in a ratio of 4:1 with an additional 1% of Et₃N. Yield: 3.7 g (64%).

Synthesis of N-(1-benzylpiperidin-4-yl)propionamide

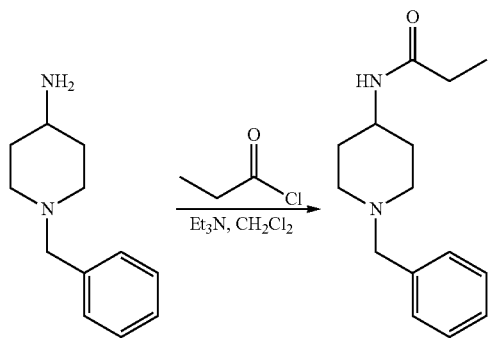

A solution of 3.7 g of 1-benzylpiperidin-4-amine (1 equiv., 0.019 mol) dissolved in 45 mL of dry dichloromethane was prepared followed by the addition of 5 mL of Et₃N (2.6 equiv., 0.05 mol). The reaction mixture was then cooled to 0° C. using an ice bath, and then 2.17 mL (1.3 equiv., 0.025 mol) of propionyl chloride dissolved in 10 mL of dry dichloromethane was added dropwise to the reaction mixture. The reaction mixture was then warmed to room temperature and stirred overnight. Once the reaction was complete, 4 mL of NH₄OH and 45 mL of H₂O were added to the reaction mixture. The organic layer was separated, and the aqueous layer was washed with dichloromethane (3×20 mL) followed by NaHCO₃ solution and brine. The organic extracts were dried over anhydrous magnesium sulfate and the solvent was removed via rotary evaporation, resulting in a white solid. The product was washed with hexanes to obtain an analytically pure sample. Yield: 2.8 g (72%)

Synthesis of N-(piperidin-4-yl)propionamide

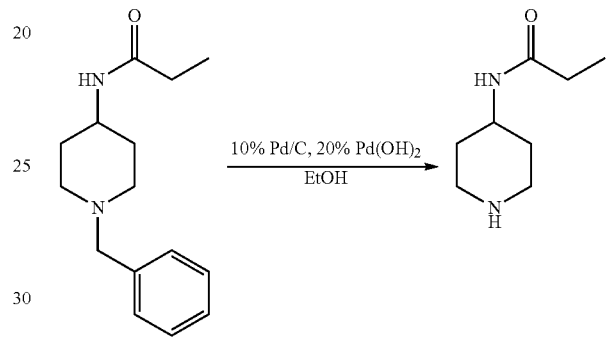

0.7 g of N-(1-benzylpiperidin-4-yl)propionamide (1 equivalent, 0.003 moles) were added to a parr hydrogenation flask and dissolved in 30 mL of EtOH. The solution was then degassed with argon for 30 min followed by the addition of 0.07 g of 10% Pd/C (0.2 equiv., 6.58×10⁻⁴ mol) and 0.07 g of 20% Pd(OH)₂ (0.17 equiv., 4.98×10⁻⁴ mol). The black solution was then degassed with argon for an additional 15 min. The reaction mixture was then charged with 50 psi of H₂ gas and shaken for 24 h. The product was filtered through celite and the solvent was removed via rotary evaporation. No further purification was required. Yield: 0.467 g (99%)

Synthesis of methyl 3-(4-propionamidopiperidin-1-yl)propanoate (CRA5)

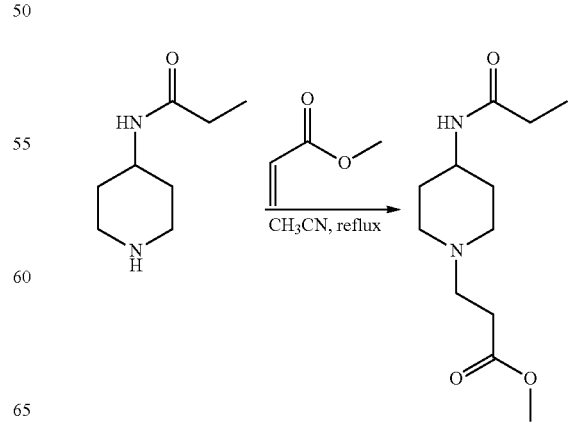

0.1 g of N-(piperidin-4-yl)propionamide (1 equiv., 5.26× $10^{-4}$ moles) was dissolved in 2 mL of dry acetonitrile followed by the addition of 0.071 mL of methyl acrylate (1.5 equiv., 7.89×$10^{-4}$ mol). The reaction mixture was refluxed overnight. The solvent was removed via rotary evaporation. The crude product was purified by washing with hexanes followed by drying under high vacuum. Yield: 0.90 g (71%)

Synthesis of N-(1-(2-(thiophen-2-yl)ethyl)piperidin-4-yl)propionamide (CRAS1)

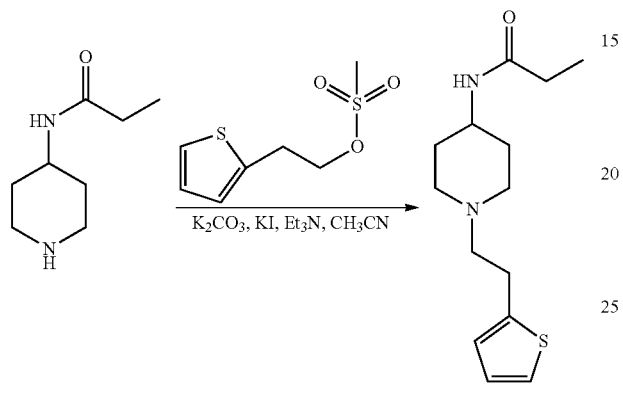

0.1 g of N-(piperidin-4-yl)propionamide (1 equiv., 6.40× $10^{-4}$ mol), 0.145 g of 2-(thiophen-2-yl)ethyl methanesulfonate (1.1 equiv., 7.04×$10^{-4}$ moles), 0.097 g of $K_2CO_3$ (1.1 equiv., 7.04×$10^{-4}$ mol), 0.032 g of KI (1.92×$10^{-4}$ mol), and 0.178 mL of $Et_3N$ (2 equiv., 1.28×$10^{-3}$ mol) were added to a round bottom flask and dissolved in 5 mL of dry acetonitrile. The reaction mixture was stirred and refluxed overnight. The solvent was then removed via rotary evaporation followed by the addition of $H_2O$. The mixture was extracted with ethyl acetate (3×5 mL), and the organic extracts were combined and dried over anhydrous magnesium sulfate. The solvent was removed via rotary evaporation. The crude product was washed with hexanes to obtain an analytically pure sample. Yield: 0.101 g (60%).

Synthesis of 1-phenethylpiperidin-4-one oxime

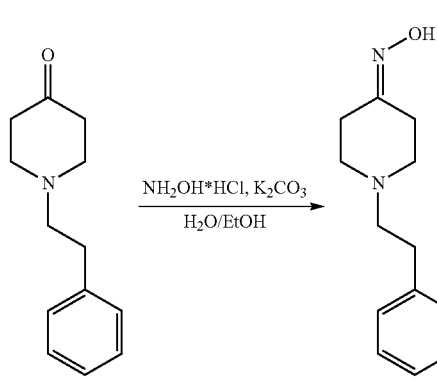

28.35 g (1 equivalent, 0.14 mol) of 1-benzylpiperidin-4-one were dissolved in 60 mL of EtOH and then cooled to 0° C. using an ice bath. A solution containing 19.46 g (2 equivalents, 0.28 mol) of hydroxylamine hydrochloride dissolved in 75 mL of $H_2O$ was prepared and then added dropwise to the reaction mixture followed by dropwise addition of a solution containing 19.35 g (1 equivalent, 0.14 mol) of $K_2CO_3$ dissolved in 75 mL of $H_2O$. The reaction mixture was then brought to room temperature and stirred overnight. The EtOH was then removed via rotary evaporation and the reaction mixture was then cooled in an ice bath to allow the product to crystallize out of solution. The product was filtered and washed several times with $H_2O$ and recrystallized in EtOH. Yield: 25.60 g (83.77%).

Synthesis of 1-phenethylpiperidin-4-amine

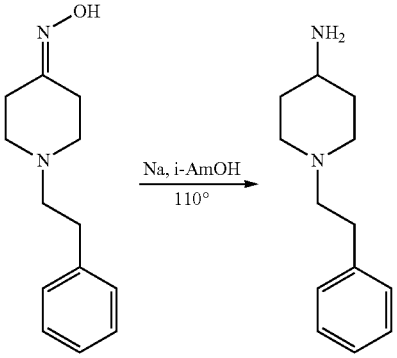 [SMILES: ON=C1CCN(CCc2ccccc2)CC1 ; NC1CCN(CCc2ccccc2)CC1]

A solution containing 6.00 g (1 equiv., 0.027 mol) of 1-phenethylpiperidin-4-one oxime dissolved in 90 mL of iso-amyl alcohol was prepared and heated to approximately 110° C. 6.21 g (10 equiv., 0.27 mol) of Na metal was then added slowly to the reaction mixture. After addition of Na, the reaction mixture was allowed to cool to room temperature and stirred until the reaction mixture turned into a thick slurry. The slurry was dissolved in 50 mL of ethyl acetate and 25 mL of $H_2O$. The organic layer was separated and washed with $H_2O$ (2×20 mL) followed by drying over anhydrous magnesium sulfate. The solvent was removed via rotary evaporation, resulting in a yellow oil. The crude product was purified via column chromatography utilizing silica gel and a DCM:MeOH solvent system in a ratio of 4:1 containing an additional 1% of $Et_3N$.

Synthesis of N-(1-phenethylpiperidin-4-yl)furan-2-carboxamide (CRA8)

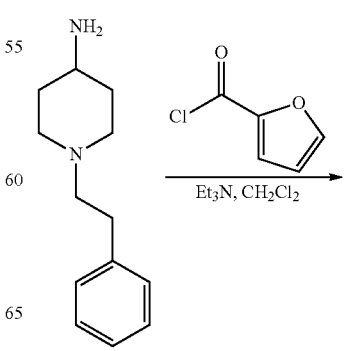

-continued

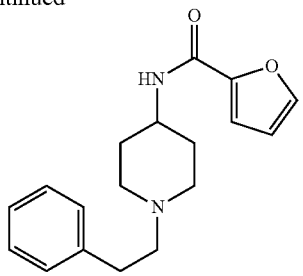

A solution of 0.1 g of 1-phenethylpiperidin-4-amine (1 equiv., 4.89×10⁻⁴ mol) dissolved in 2 mL of dry dichloromethane was prepared followed by the addition of 0.178 mL (2.6 equiv., 1.27×10⁻³ moles) of Et$_3$N. The reaction mixture was then cooled to 0° C. using an ice bath, and then 0.063 mL (1.3 equiv., 6.36×10⁻⁴ mol) of 2-furoyl chloride dissolved in 0.25 mL of dry dichloromethane was added dropwise to the reaction mixture. The reaction mixture was then warmed to room temperature and stirred overnight. Once the reaction was complete, 4 mL of NH$_4$OH and 45 mL of H$_2$O were added to the reaction mixture. The organic layer was separated, and the aqueous layer was washed with dichloromethane (3×5 mL) followed by NaHCO$_3$ solution and brine. The organic extracts were dried over anhydrous magnesium sulfate and the solvent was removed via rotary evaporation, resulting in a white solid. The product was washed with hexanes to obtain an analytically pure sample. Yield: 0.0845 g (58.3%).

Synthesis of
N-(1-phenethylpiperidin-4-yl)furan-3-carboxamide
(CRA9)

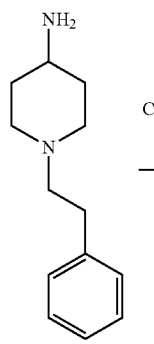
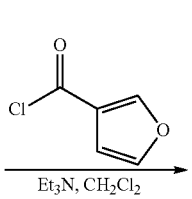

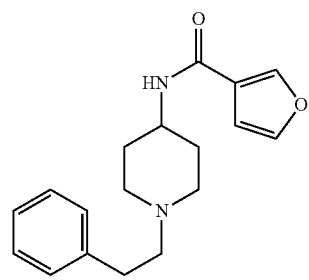

A solution of 0.1 g of 1-phenethylpiperidin-4-amine (1 equiv., 4.89×10⁻⁴ mol) dissolved in 2 mL of dry dichloromethane was prepared followed by the addition of 0.178 mL (2.6 equiv., 1.27×10⁻³ mol) of Et$_3$N. The reaction mixture was then cooled to 0° C. using an ice bath, and then 0.063 mL (1.3 equiv., 6.36×10⁻⁴ mol) of 3-furoyl chloride dissolved in 0.25 mL of dry dichloromethane was added dropwise to the reaction mixture. The reaction mixture was then warmed to room temperature and stirred overnight. Once the reaction was complete, 4 mL of NH$_4$OH and 45 mL of H$_2$O were added to the reaction mixture. The organic layer was separated, and the aqueous layer was washed with dichloromethane (3×5 mL) followed by NaHCO$_3$ solution and brine. The organic extracts were dried over anhydrous magnesium sulfate and the solvent was removed via rotary evaporation, resulting in a white solid. The product was washed with hexanes to obtain an analytically pure sample. Yield: 0.104 g (72%).

Synthesis of
8-bromo-N-(1-phenethylpiperidin-4-yl)octanamide
(CRA10)

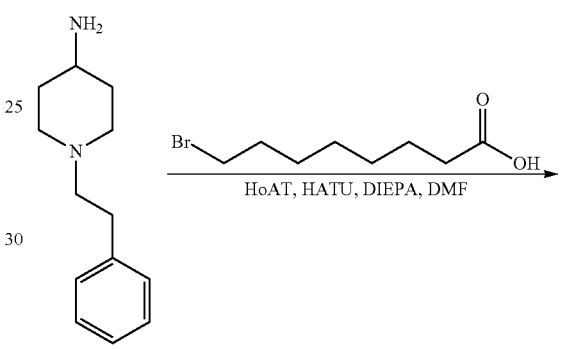

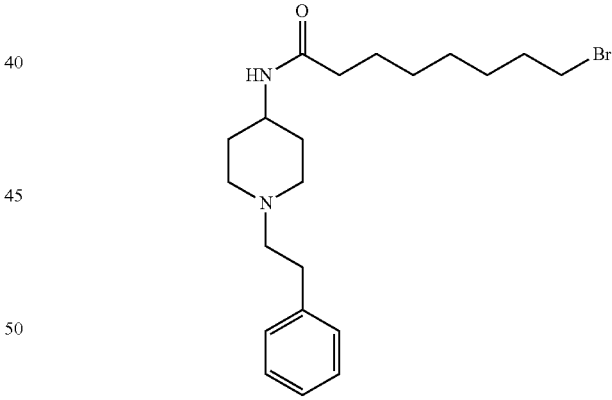

A solution of 0.101 g of 1-phenethylpiperidin-4-amine (1.1 equiv., 4.93×10⁻⁴ mol), 0.1 g of 8-bromooctanoic acid (1.0 equiv., 4.48×10⁻⁴ mol), 0.170 g of HATU (1.0 equiv., 4.48×10⁻⁴ mol), 0.061 g of HOAt (1.0 equiv., 4.48×10⁻⁴ mol), and 0.314 mL of DIEPA (4.0 equiv., 0.0018 mol) in dry DMF was prepared. The reaction mixture was stirred at room temperature overnight. The reaction mixture was then quenched with 0.5 M KHSO$_4$ solution followed by the addition of dichloromethane. The organic and aqueous layers were separated, and the aqueous layer was extracted with dichloromethane (3×5 mL) followed by washing with NaHCO$_3$ solution and Brine. The organic extracts were then dried over anhydrous magnesium sulfate.

Synthesis of N-(1-phenethylpiperidin-4-yl)benzamide (CRA11)

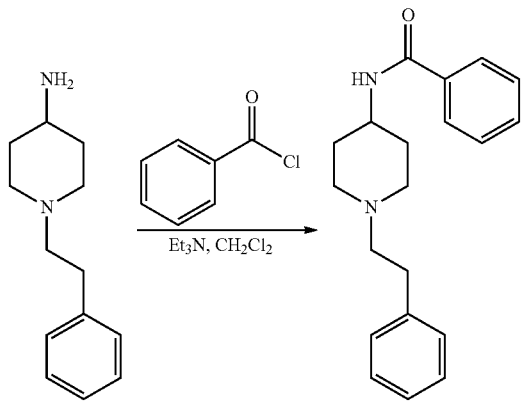

A solution of 0.1 g of 1-phenethylpiperidin-4-amine (1 equiv., 4.89×10$^{-4}$ mol) dissolved in 2 mL of dry dichloromethane was prepared followed by the addition of 0.178 mL (2.6 equiv., 1.27×10$^{-3}$ mol) of Et$_3$N. The reaction mixture was then cooled to 0° C. using an ice bath, and then 0.074 mL (1.3 equiv., 6.36×10$^{-4}$ mol) of 3-furoyl chloride dissolved in 0.25 mL of dry dichloromethane was added dropwise to the reaction mixture. The reaction mixture was then warmed to room temperature and stirred overnight. Once the reaction was complete, 4 mL of NH$_4$OH and 45 mL of H$_2$O were added to the reaction mixture. The organic layer was separated, and the aqueous layer was washed with dichloromethane (3×5 mL) followed by NaHCO$_3$ solution and brine. The organic extracts were dried over anhydrous magnesium sulfate and the solvent was removed via rotary evaporation, resulting in a white solid. The product was washed with hexanes to obtain an analytically pure sample.

Synthesis of 2-(thiophen-2-yl)ethyl methanesulfonate

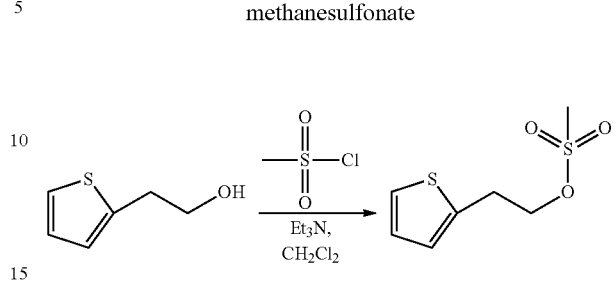

2.6 mL of 2-(thiophen-2-yl)ethanol (1 equiv., 0.023 mol) was dissolved in 45 mL of dry dichloromethane followed by the addition of 3.63 mL of Et$_3$N (1.13 equiv., 0.026 mol). The reaction mixture was stirred at room temperature for 1 h. It was then cooled to -5° C. using an ice bath and solid NaCl. Once cooled, 1.92 mL of methanesulfonyl chloride was added dropwise over the course of 10 min. The reaction mixture was then warmed to room temperature and stirred for 1 h. Once the reaction was complete, 30 mL of NaHCO$_3$ solution was added followed by separation of the organic and aqueous layers. The aqueous layer was extracted with dichloromethane (3×30 mL). The combined organic extracts were dried over anhydrous magnesium sulfate and the solvent was removed via rotary evaporation, resulting in a brown oil. No further purification was required.

NMR ($^1$H & $^{13}$C) & Mass-Spec Data of Novel Substituted 1-arylethyl-4-acylaminopiperidine Derivatives (Total Six Compounds)

| Compound | Molecular Formula | Structure | R$_f$ | Exact Mass | Observed Mass [M + H]$^+$ | Yield |
|---|---|---|---|---|---|---|
| CRA5 | C$_{12}$H$_{22}$N$_2$O$_3$ | 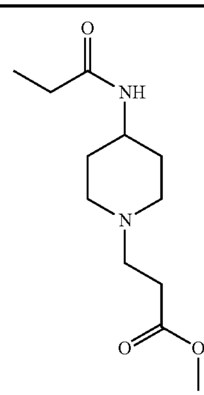 | 0.72 (20% MeOH in DCM) | 242.16 | 243.3 | 90 mg (70.7%) |
| CRA8 | C$_{18}$H$_{22}$N$_2$O$_2$ | 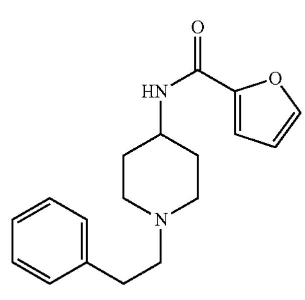 [SMILES: O=C(NC1CCN(CCc2ccccc2)CC1)c1ccco1] | 0.825 (4:1 MeOH DCM) | 298.17 | 299.3 | 84.5 mg (58.3%) |

-continued

| Compound | Molecular Formula | Structure | $R_f$ | Exact Mass | Observed Mass [M + H]$^+$ | Yield |
|---|---|---|---|---|---|---|
| CRA9 | C$_{18}$H$_{22}$N$_2$O$_2$ | 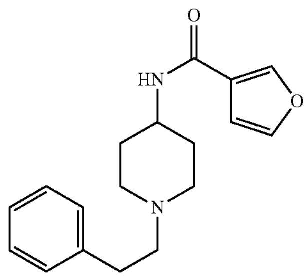 [SMILES: O=C(NC1CCN(CCc2ccccc2)CC1)c1ccoc1] | 0.757 (4:1 MeOH DCM) | 298.17 | 299.3 | 104.3 mg (71.9 %) |
| CRAS1 | C$_{14}$H$_{22}$N$_2$OS | 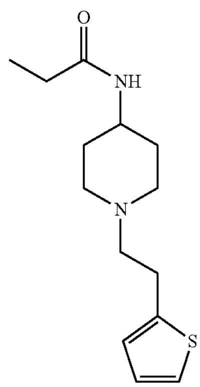 [SMILES: CCC(=O)NC1CCN(CCc2cccs2)CC1] | | 266.15 | 267.73 | 101.4 mg (60%) |
| CRA10 | C$_{21}$H$_{33}$BrN$_2$O | 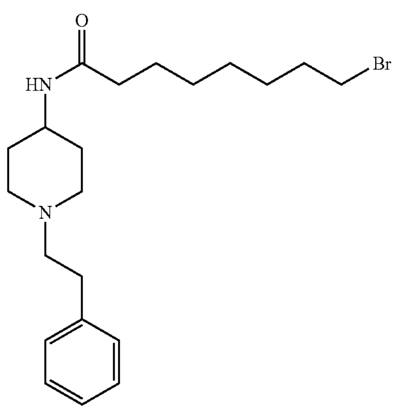 [SMILES: O=C(CCCCCCCBr)NC1CCN(CCc2ccccc2)CC1] | 0.90 | 408.18 | 409.19 411.19 | 262 mg (130%) |
| CRA11 | C$_{20}$H$_{24}$N$_2$O | 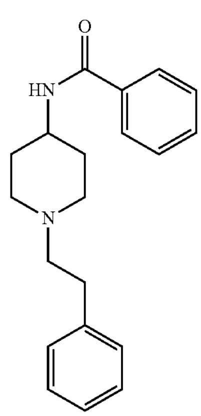 [SMILES: O=C(NC1CCN(CCc2ccccc2)CC1)c1ccccc1] | 0.875 | 308.19 | 309.2 | 132 mg (87%) |

CRA5 NMR data: $^1$H NMR (400 MHz, CDCl$_3$) δ 1.14 (t, J=7.59, 7.59 Hz, 3H), 1.41 (dtd, J=3.70, 11.10, 11.13, 12.61 Hz, 2H), 1.91 (m, 2H), 2.17 (m, 4H), 2.49 (m, 2H), 2.68 (m, 2H), 2.81 (m, 2H), 3.67 (s, 3H), 3.78 (dddd, J=4.29, 4.36, 11.92, 15.26, 1H), 5.25 (d, J=7.96 Hz, 1H). $^{13}$C NMR (100 MHz, CDCl$_3$) δ 10.02, 29.99, 32.41, 46.40, 51.76, 52.25, 55.63, 173.14, 174.05.

CRA8 NMR data: $^1$H NMR (400 MHz, CDCl$_3$) δ 1.63 (d, J=11.93 Hz, 2H), 2.05 (d, J=12.33 Hz, 2H), 2.26 (t, J=11.35, 11.35 Hz, 2H), 2.64 (dd, J=6.16, 10.21 Hz, 2H), 2.83 (dd, J=6.12, 10.24 Hz, 2H), 2.99 (d, J=12.01 Hz, 2H), 3.98 (m, 1H), 6.21 (d, J=8.20 Hz, 1H), 6.49 (dd, J=1.79, 3.47 Hz, 1H), 7.10 (dd, J=0.84, 3.47 Hz, 1H), 7.24 (m, 5H), 7.43 (dd, 0.84, 1.77 Hz, 1H). $^{13}$C NMR (100 MHz, CDCl$_3$) δ 32.67, 34.17, 46.27, 46.61, 52.76, 60.88, 112.60, 114.57, 126.56, 128.87, 129.13, 140.58, 144.16, 148.48, 158.13.

CRA9 NMR data: $^1$H NMR (400 MHz, CDCl$_3$) δ 1.63 (m, 2H), 2.06 (d, J=11.35 Hz, 2H), 2.26 (m, J=11.35, 2H), 2.65 (m, 2H), 2.84 (m, 2H), 3.02 (d, J=11.86 Hz, 2H), 3.99 (m, 1H), 5.65 (d, J=7.99 Hz, 1H), 6.59 (dd, J=0.91, 1.93 Hz, 1H), 7.24 (m, 5H), 7.42 (dd, 1.58, 1.91 Hz, 1H), 7.91 (dd, J=0.90, 1.59 Hz, 1H). $^{13}$C NMR (100 MHz, CDCl$_3$) δ 32.04, 33.49, 46.43, 52.35, 60.26, 108.25, 122.66, 126.19, 128.46, 128.68, 139.88, 143.72, 144.69, 161.95

CRA1S NMR data: $^1$H NMR (400 MHz, CDCl$_3$) δ 1.15 (t, J=7.58, 7.58 Hz, 3H), 1.47 (m, 2H), 1.95 (m, 2H), 2.18 (m, 4H), 2.64 (dd, J=6.87, 8.62 Hz, 2H), 2.90 (m, 2H), 3.00 (m, 2H), 3.82 (dddd, J=4.20, 8.31, 10.86, 15.17 Hz, 1H), 5.32 (d, J=7.95 Hz, 1H), 6.81 (dq, J=1.02, 1.02, 1.02, 3.20 Hz, 1H), 6.91 (dd, J=3.39, 5.14 Hz, 1H), 7.11 (dd, J=1.21, 5.13 Hz, 1H). $^{13}$C NMR (100 MHz, CDCl$_3$) δ 10.04, 28.06, 30.03, 32.15, 46.52, 52.42, 59.98, 123.62, 124.71, 126.69, 142.87, 173.15.

CRA10 NMR data: $^1$H NMR (400 MHz, CDCl$_3$) δ 1.32-2.34 (m, 14H), 2.82-3.01 (m, 11H), 3.16 (dd, J=6.53, 10.91 Hz, 1H), 3.49 (d, J=11.91 Hz, 1H), 4.63 (dt, J=5.61, 5.61, 8.76 Hz, 1H), 7.24 (m, 4H), 7.42 (dd, J=4.46, 8.37, 1H), 8.02 (m, 1H). $^{13}$C NMR (100 MHz, CDCl$_3$) δ 25.17, 25.45, 27.85, 28.70, 28.75, 31.46, 36.55, 38.61, 81.47, 120.73, 128.66, 128.86, 129.19, 151.29, 162.71, 173.62.

CRA11 NMR data: $^1$H NMR (400 MHz, CDCl$_3$) δ 1.35 (t, J=7.29, 7.29 Hz, 2H), 1.64 (qd, J=3.80, 11.29, 11.29, 11.35 Hz, 2H), 2.08 (m, 2H), 2.27 (td, J=2.57, 11.61, 11.65 Hz, 2H), 2.64 (m, 2H), 2.83 (m, 2H), 3.00 (m, 3H), 4.04 (dddd, J=4.28, 8.29, 10.85, 15.24 Hz, 1H), 6.04 (d, J=7.94 Hz, 1H), 7.25 (m, 5H), 7.44 (m, 3H), 7.75 (m, 2H). $^{13}$C NMR (100 MHz, CDCl$_3$) δ 32.22, 33.71, 45.83, 46.97, 52.38, 60.42, 114.25, 126.12, 126.86, 128.42, 128.56, 128.68, 131.42, 134.75, 140.11, 166.88

Many other variations and modifications may be made to the above-described embodiments of the disclosure without departing substantially from the spirit and principles of the disclosure. All such modifications and variations are intended to be included herein within the scope of the present disclosure and protected by the following claims.

Literature Cited

1. Thayer, A., Drugs To Fight Addictions, Chem. Eng. News, (2006), 84(39), 21-44.
2. Heidbreder, C., Novel pharmacotherapeutic targets for the management of drug addiction, Eur. J. Pharmacol., (2005), 526 (1-3), 101-112.
3. Woods, J. H., Traynor, J. R., Evaluation of new compounds for opioid activity (2000), NIDA Research Monograph, Volume Date 2000, 181 (Problems of Drug Dependence 2000), (2001), 140-155.
4. Husbands, S. M., Lewis, J. W., Opioid ligands having delayed long-term antagonist activity: Potential pharmacotherapies for opioid abuse, Mini-Revi. Med. Chem., (2003), 3(2), 137-144.
5. Schmidhammer, H., Opioid receptor antagonists, Prog. Med. Chem., (1998), 35, 83-132.
6. Boothby, L. A., Doering, P. L., Buprenorphine for the treatment of opioid dependence, Am. J. Health-System Pharm., (2007), 64(3), 266-272.
7. Lowengrub, K., Iancu, I., Aizer, A., Kotler, M., Dannon, P. N., Pharmacotherapy of pathological gambling: review of new treatment modalities, Exp. Rev. Neurotherapeut., (2006), 6(12), 1845-1851.
8. Krishnan-Sarin, S., O'Malley, S. S., Opioid antagonists for the treatment of nicotine dependence, Med. Treat. Nicotine Depend., (2007) 123-135.
9. White, J. M., Lopatko, O. V., Opioid maintenance: a comparative review of pharmacological strategies, Expert Opin. Pharmacotherapy, (2007), 8(1), 1-11.
10. Cunningham, C. W., Coop, A., Therapeutic applications of opioid antagonists, Chimica Oggi, 24(3), 54-57 (2006).
11. Lauretti, G. R., Highlights in opioid agonists and antagonists, Expert Rev. Neurotherapeut., 6(4), 613-622 (2006).
12. Capasso, A., D'Ursi, A., Pharmacological activity of new mu, k, delta receptor agonists and antagonists. Studies in Natur. Prod. Chem. (2005), 30, 797-823.
13. Anon, N. Z., Alvimopan: ADL 8-2698, ADL 82698, entrareg, L Y 246736, Drugs in R&D, (2006), 7(4), 245-253.
14. Leslie, J. B., Alvimopan: a peripherally acting Mu-. Opioid receptor antagonists, Drugs of Today (2007), 43(9), 611-625.
15. Goodman, A. J.; Le Bourdonnec, B.; Dolle, R. E. Mu opioid receptor antagonists: recent developments, ChemMedChem (2007), 2(11), 1552-1570.
16. Taylor, R., Jr.; Pergolizzi, J. V., Jr.; Porreca, F.; Raffa, R. B. Opioid antagonists for pain Exp. Opin. Invest. Drugs, (2013), 22(4), 517-525.
17. Hipkin, R. W.; Dolle, Roland E., Opioid receptor antagonists for gastrointestinal dysfunction, Ann. Rep. Med. Chem., (2010), 45, 143-155.
18. Stotts, A. L.; Dodrill, C. L.; Kosten, T. R. Opioid dependence treatment: options in pharmacotherapy, Exp. Opin. Pharmacother., (2009), 10(11), 1727-1740.
19. Soyka, M.; Roesner, S., Opioid antagonists for pharmacological treatment of alcohol dependence—a critical review, Curr. Drug Abuse Rev., (2008), 1(3), 280-291.
20. Hopp, M.; Trenkwalder, C., Combination of opioid agonists and opioid antagonists for the treatment of Parkinson's disease and associated symptoms, WO 2012089738 (2012).
21. Mouradian, M. M.; Braithwaite, S.; Voronkov, M., Method of treating dyskinesia using dual-action mu-opioid receptor antagonist/kappa-opioid receptor agonist or prodrug thereof, WO 2012149113 (2012).
22. Bosco, D.; Plastino, M.; Colica, C.; Bosco, F.; Arianna, S.; Vecchio, A.; Galati, F.; Cristiano, D.; Consoli, A.; Consoli, D., Opioid Antagonist Naltrexone for the Treatment of Pathological Gambling in Parkinson Disease, Clinical Neuropharmacology (2012), 35(3), 118-120.
23. Henry, B.; Brotchie, J. M., Potential of opioid antagonists in the treatment of levodopa-induced dyskinesias in Parkinson's disease (A review and discussion), Drugs & Aging (1996), 9(3), 149-158.

24. Buck, K.; Ferger, B., The selective αl adrenoceptor antagonist HEAT reduces L-DOPA-induced dyskinesia in a rat model of Parkinson's disease, Synapse (2010), 64(2), 117-126.
25. Lewitt P. A; Hauser R. A; Lu M.; Nicholas A. P.; Weiner W.; Coppard N.; Leinonen M.; Savola J.-M., Randomized clinical trial of fipamezole for dyskinesia in Parkinson disease (FJORD study), Neurology (2012), 79(2), 163-9.
26. Brefel-Courbon, C.; Thalamas, C.; Paul, H. P. S.; Senard, J-M.; Montastruc, J-L.; Rascol, O., α2-Adrenoceptor antagonists. A new approach to Parkinson's disease? CNS Drugs (1998), 10(3), 189-207.
27. Millan M. J., From the cell to the clinic: a comparative review of the partial D2/D3 receptor agonist and α2-adrenoreceptor antagonists, piribedil, in the treatment of Parkinson's disease Pharmacol. Therapeut. (2010), 128 (2), 229-73.
28. 14. Kaczor, A., Matosiuk, D., Non-peptide opioid receptor ligands—recent advances. Part II. Antagonists, Carr. Med. Chem., (2002), 9(17), 1591-1603.
29. 15. Zimmerman, D. M., Leander, J. D., Opioid antagonists: structure activity relationships, NIDA Research Monograph, (1990), 96, 50-60 (1990).
30. Lauretti, G. R., Highlights in opioid agonists and antagonists, Exp. Rev., Neurotherapeut., (2006), 6(4), 613-622 (2006).
31. van Dorp, E. L. A., Yassen, A., Dahan, A., Naloxone treatment in opioid addiction: the risks and benefits, Exp. Opin. Drug Safety, (2007), 6(2), 125-132.
32. Comer, S. D., Sullivan, M. A, Hulse, G. K., Sustained-release naltrexone: novel treatment for opioid dependence, Exp. Opin. Invest. Drugs, (2007), 16(8), 1285-1294.
33. Boothby, L. A., Doering, P. L., Buprenorphine for the treatment of opioid dependence, Am. J. Health-Syst. Pharm., (2007), 64(3), 266-272.
34. Raisch, D. W., Fye, C. L., Boardman, K. D., Sather, M. R. Opioid dependence treatment, including buprenorphine/naloxone. Annals Pharmacother., (2002), 36(2), 312-321.
35. White, J. M., Lopatko, O. V., Opioid maintenance: a comparative review of pharmacological strategies, Exp. Opin. Pharmacother., (2007), 8(1), 1-11.
36. Roozen, H. G., de Waart, R., van der Windt, D. A. W. M., van den Brink, W., de Jong, C. A. J., Kerkhof, A. J. F. M., A systematic review of the effectiveness of naltrexone in the maintenance treatment of opioid and alcohol dependence, Eur. Neuropsychopharmacol., (2006), 16(5), 311-323.
37. Schmidhammer, H., Opioid receptor antagonists, Progr. Med. Chem., (1998), 35, 83-132.
38. Yuan, C.-S., Israel, R. J., Methylnaltrexone, a novel peripheral opioid receptor antagonist for the treatment of opioid side effects, Exp. Opin. Invest. Drugs, (2006), 15(5), 541-552.
39. Comer, S. D., Sullivan, M. A., Hulse, Gary K., Sustained-release naltrexone: novel treatment for opioid dependence, Exp. Opin. Invest. Drugs, (2007), 16(8), 1285-1294.
40. Eguchi, M., Recent advances in selective opioid receptor agonists and antagonists, Med. Res. Rev., (2004), 24(2), 182-212.
41. Portoghese, P. S., Selective nonpeptide opioid antagonists, Handbook of Experimental Pharmacology, (1993), 104/1(Opioids I), 279-93.
42. Takemori, A. E., Portoghese P S Selective naltrexone-derived opioid receptor antagonists, Ann. Rev. Pharm. Tox., (1992), 32, 239-69.
43. Portoghese, P. S., Bivalent ligands and the message-address concept in the design of selective opioid receptor antagonists, Trends Pharm. Sci., (1989), 10(6), 230-5.
44. Portoghese, P. S., The design of delta-selective opioid receptor antagonists, Farmaco, (1993), 48(2), 243-51.
45. Metcalf, M. D., Coop A., Kappa opioid antagonists: past successes and future prospects, The AAPS J., (2005), 7(3), E704-22.
46. Furst, S., Hosztafi, S., Friedmann, T., Structure-Activity Relationships of Synthetic and Semisynthetic Opioid Agonists and Antagonists, Curr. Med. Chem., (1995), 1, 423-40.

INCORPORATION BY REFERENCE

Each document, patent, patent application or patent publication cited by or referred to in this disclosure is incorporated by reference in its entirety. However, no admission is made that any such reference constitutes prior art, and the right to challenge the accuracy and pertinence of the cited documents is reserved.

The invention claimed is:

1. A compound of the formula:

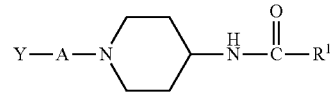

or a pharmaceutically acceptable salt thereof,
wherein
$R^1$ is selected from the group consisting of optionally substituted $C_{1-10}$ alkyl, and optionally substituted furanyl;
A is ethylene; and
Y is selected from the group consisting of unsubstituted aryl, optionally substituted thiophenyl, or a moiety of the formula —C(═O)—$X^1$, wherein $X^1$ is —$OR^5$ or —$NR^6R^6$, wherein each of $R^5$ and $R^6$ is H or $C_{1-10}$ alkyl.

2. The compound of claim 1, wherein $R^1$ is selected from the group consisting of ethyl, 7-bromoheptyl, fur-2-yl, and fur-3-yl.

3. The compound of claim 1, wherein Y is selected from the group consisting of phenyl, thiophen-2-yl, and a moiety of the formula —C(═O)—$OR^5$, wherein $R^5$ is $C_{1-10}$ alkyl.

4. The compound of claim 1 selected from the group consisting of:
N-(1-phenethylpiperidin-4-yl)propionamide;
methyl 3-(4-propionamidopiperidin-1-yl)propanoate;
N-(1-phenethylpiperidin-4-yl)furan-2-carboxamide;
N-(1-phenethylpiperidin-4-yl)furan-3-carboxamide;
N-(1-(2-(thiophen-2-yl)ethyl)piperidin-4-yl)propionamide; and
8-bromo-N-(1-phenethylpiperidin-4-yl)octanamide.

5. A method of treating a condition selected from opioid tolerance and dependence, opioid-induced constipation, alcohol abuse, opioid abuse, cocaine abuse, depression, opioid induced immune response depression, opioid-overdose-induced respiratory depression, nicotine withdrawal symptoms, obesity, psychosis, dyskinesia associated with Parkinson's disease, Raynaud's disease, hypertension, scleroderma or a combination thereof, said method comprising administering a therapeutically effective amount of a compound of claim 1 to a subject in need of such a treatment.

6. The method claim 5, wherein said clinical condition is dyskinesia associated with Parkinson's disease.

7. A compound of the formula:

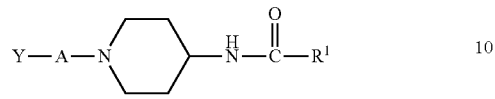

or a pharmaceutically acceptable salt thereof, wherein $R^1$ is selected from the group consisting of optionally substituted $C_{1-10}$ alkyl, and optionally substituted furanyl;

A is $C_{1-10}$ alkylene; and

Y is selected from the group consisting of phenyl, thiophen-2-yl, and a moiety of the formula —C(=O)—OR$^5$, wherein $R^5$ is $C_{1-10}$ alkyl.

8. The compound of claim 7, wherein $R^1$ is selected from the group consisting of ethyl, 7-bromoheptyl, fur-2-yl, and fur-3-yl.

9. The compound of claim 8, wherein $R^1$ is ethyl.

10. The compound of claim 7, wherein A is ethylene.

11. The compound of claim 10, wherein Y is phenyl.

* * * * *